United States Patent
Burdsall et al.

(10) Patent No.: US 7,167,166 B1
(45) Date of Patent: Jan. 23, 2007

(54) METHOD AND SYSTEM FOR PROCESSING OBSERVATION CHARTS

(75) Inventors: Ben Burdsall, Opio (FR); Ivan Montet, Valbonne (FR)

(73) Assignee: Accenture Global Services GmbH, Schaffhausen (CH)

( * ) Notice: Subject to any disclaimer, the term of this patent is extended or adjusted under 35 U.S.C. 154(b) by 420 days.

(21) Appl. No.: 10/632,588

(22) Filed: Aug. 1, 2003

(51) Int. Cl.
G09G 5/00 (2006.01)

(52) U.S. Cl. .................. 345/179; 345/156; 178/18.01; 178/19.01; 178/19.05

(58) Field of Classification Search ................ 345/179, 345/156; 178/18.01, 19.01, 19.05
See application file for complete search history.

(56) References Cited

U.S. PATENT DOCUMENTS

| | | | | |
|---|---|---|---|---|
| 4,457,312 | A * | 7/1984 | Ornato et al. | 600/524 |
| 5,758,095 | A * | 5/1998 | Albaum et al. | 705/2 |
| 6,198,383 | B1 * | 3/2001 | Sekura et al. | 340/309.4 |
| 6,603,464 | B1 * | 8/2003 | Rabin | 345/179 |
| 2004/0019879 | A1 * | 1/2004 | Segawa et al. | 717/124 |

FOREIGN PATENT DOCUMENTS

| | | |
|---|---|---|
| WO | WO 01/26032 A1 | 4/2001 |
| WO | WO 01/26033 A1 | 4/2001 |
| WO | WO 01/26034 A1 | 4/2001 |
| WO | WO 01/48685 A1 | 7/2001 |
| WO | WO 03/038741 A1 | 5/2003 |
| WO | WO 03/042907 A1 | 5/2003 |
| WO | WO 03/042912 A1 | 5/2003 |

\* cited by examiner

*Primary Examiner*—Richard Hjerpe
*Assistant Examiner*—Leonid Shapiro
(74) *Attorney, Agent, or Firm*—Brinks Hofer Gilson & Lione

(57) ABSTRACT

The invention concerns a method and system for digitally processing information to be written on an observation form, said form being preprinted with at least one blank chart having at least one line and several columns, each column corresponding to a determined printed time, said form being also preprinted with a pattern adapted to cooperate with a digital pen and a computerized localization system for determining the position of the pen; using a pen having a writing tip and a digital tip; filling in data in one column at a time; reproducing said data in the computerized localization system and associating to said data its recording time; and comparing said recording time with the localized printed time of said data, so as to detect any inconsistency between the recording time and the printed time.

19 Claims, 1 Drawing Sheet

METHOD AND SYSTEM FOR PROCESSING OBSERVATION CHARTS

FIELD OF INVENTION

The present invention relates to a method and system for digitally registering and processing observation charts, especially in the medical field.

BACKGROUND OF THE INVENTION

Observation charts are conventionally paper or cardboard sheets used for monitoring the health of a patient. A single sheet or form may contains several charts monitoring different parameters such as temperature, pulse, blood pressure, respiration, drug administration, etc. Most of these charts are time scaled. Observation charts are important sources of information for the successive nurses and doctors taking in charge a same patient during his stay in a hospital.

Usually, the observation charts are preprinted forms with blank charts forming a squaring, each line or gap between two lines in one direction (usually the vertical one defining columns) corresponding to a determined time or a determined time period. Lines of different thickness may outline the scale of the time. The scale of the other axis of each chart corresponds to the monitored parameter (degrees, number, etc.). Sometimes, this parameter scale is not preprinted and is to be completed by the medical staff. Further, some charts may contain a single row when the required information only corresponds to the time of an action (for example, drug administration, visit of the doctor, etc.). The forms also contain boxes or analog to be filled with other information, such as the identity of the patient, the identity of the medical staff, etc.

Conventionally, the observation forms are filled in manually by the doctors or nurses. For the time scaled charts, a dot or cross is written at the location corresponding to the time (at the intersection between a printed time and parameter level for the charts having scale in both axes). For scaled parameters like the temperature, a link line may joint the successive dots.

Recently, computerized systems have been proposed to be substituted for conventional observation forms. Such systems have the advantage of allowing a digital storage and processing of the data. However, these systems require a keyboard, a sensitive screen or the like as input device, and a display screen for displaying the information to the medical staff.

A problem resides in the fact that the observation forms have to be attached to the beds of the patients or in close proximity to the beds to be consultable at any time by the medical staff. Such a requirement renders the conventional computerized systems inapplicable as it is unrealistic, among others for cost purposes, to propose a system in which each bed of a hospital is provided with a screen or the like.

Another problem with computerized systems is that it usually complicates registering information. In particular, the observation forms are to be updated periodically and during a relative long period of time (one week or more). Hence, it is not desirable to multiply the number of additional steps with respect to handwriting.

SUMMARY OF THE INVENTION

A purpose of the present invention is to provide a method and system for digitally registering and processing observation forms without suppressing the local visualization of the forms.

Another purpose of the invention is to improve the reliability of charts of observation forms especially for detecting eventual timing errors. In particular, the invention aims at providing automatic alerts in case of inconsistent handwriting on a chart.

Another purpose of the invention is to provide an automatic detection of missed action. Especially, the invention aims to detect when a drug administration form has not been updated in a timely manner indicating, for example, that a patient has not had his drug administered.

Another purpose of the invention is to improve the efficiency of the drug stock management of a hospital or the like on the basis of the drug prescriptions.

To attain these purposes and others, the present invention uses a digital pen for filling observation forms containing time scaled observation charts. As conventional in such a technology, a specific coding pattern comprising dots or marks is printed in background of a paper sheet so that a computerized localization system can determine the position (x, y coordinates) of a digital pen on the sheet. The digital pen has the global shape of a usual pen, comprises an IR camera built in a pressure sensor and further comprises a usual tip. The localization system localizes the tip by recognizing the position code on the sheet. Taking into account the displacements of the pen renders possible the localization even without initializing the position of the pen. Usually, the pen registers in a local memory the viewed codes along with the displacements of the tip on the sheet. Then, the pen is placed in a socket with which it communicates through a dedicated connector. The socket is linked to a computer, either directly or via an electronic network, in order to transfer the content of the local memory to the computer, which calculates the x, y coordinates of each point of the written text. Alternatively, the pen communicates directly with a computerized system through a wireless link. The registered displacements are then processed by the computer to be transformed into graphic information onto a digital reproduction of the sheet. Such a technique allows registering handwriting. Examples of such systems are disclosed in the documents WO-A-01/048685, WO-A-01/026032, WO-A-01/026033, WO-A-01/026034, WO-A-03/038741, WO-A-03/042907 and WO-A-03/042912 hereby incorporated by references.

According to the present invention, a pattern adapted to cooperate with a digital pen and a computerized localization system for determining the x, y coordinates of handwritten information is preprinted in background of forms on which are also printed, among others, blank observation charts. The blank charts can be printed along with the specific pattern required by the digital pen system. Then, the forms are used conventionally for handwriting information and, according to the invention, for converting the written data (more precisely, the optically detected displacements of the pen) into digital data usable by the computerized system. Hence, the written information is not only registered into a digital form but remains also locally visible where it is required (for example, attached to the bed of a patient in a hospital).

The digital data can be used to be superimposed to a representation of the form registered in the computerized system and displayed on a screen. Further, the digital data are stored on any conventional storage media for docketing purposes.

The areas (blank charts, blocks, etc.) printed onto the physical support (sheet, cardboard, etc.) depend on the application of the invention. Even in the medical field, various kinds of observation forms can be provided. The invention does not involve modifying the existing printed observation forms. The only requirements are that these forms are printed on (or with) a specific pattern adapted to the digital pen system and that each sheet of paper (support) to be used is, once ready for use, identifiable not only with respect to other kinds of observation forms but also with respect to other observation forms of the same kind. According to the invention, individualizing the patterns printed in background for each sheet of a same form serves to identify the filled forms from each other (hence the patients).

According to the present invention, the localization of the written data on time scaled charts serves, among others, to determine the printed time, i.e. the time associated with the column wherein, or on which, the data is written.

According to a first aspect of the present invention, the recording time of data (i.e. the time at which data is written and recorded by the pen) is stored along with its location (coordinates). Then, the recording time is compared to the localized printed time, i.e. the position on the x-axis on the medical graph. The comparison detects an eventual inconsistency between the two times. Such detection can be automatically processed with respect to a threshold of acceptable error in order, for example, to generate an alert to the medical staff. The threshold is predetermined and several different thresholds can be used depending on the kind of information (the kind of parameter monitored by the chart).

According to a second aspect of the invention, the recording time and/or the written time (localized printed time) are used to check that an action has been correctly taken with respect to a registered prescription. According to this aspect, the system automatically detects that a drug dispensing action has not been reported onto the form. Such defect of report can signify that the action has not been taken or has been taken but at an incorrect time. The system generates an alert to the medical staff or any dedicated person.

According to a preferred embodiment of the second aspect of the present invention, the writing/recording time of handwritten data relative to a drug administration is compared to the prescription in order to automatically check the drug administration. According to this aspect, the drug prescriptions are stored in the system in an interpretable way (for example, by automatically interpreting a time scaled prescription chart of a form processed according to the invention).

A time scaled prescription chart can be automatically interpreted for the ordering and stock surveying of drugs. The drug prescriptions of several patients are then collected and processed together to establish in real time order lists of drug. The ordering of the drugs can then be made, either manually or automatically, to the suppliers in a way optimizing the stocks. In particular, it is hence possible to minimize the number of drugs to be wasted for overtaking of the date of limit of use.

BRIEF DESCRIPTION OF THE DRAWINGS

The foregoing and others purposes, features, aspects and advantages of the invention will become apparent from the following detailed description of embodiments, given by way of illustration and not limitation with reference to the accompanying drawings.

DETAILED DESCRIPTION OF THE INVENTION

Figure 1:
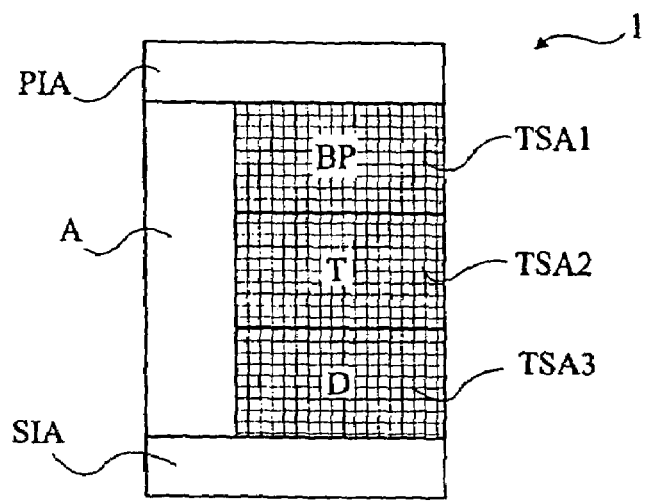
FIG. 1 illustrates a form used according to the present invention.

FIG. 1 illustrates an example of a conventional observation form 1 comprises three time scaled areas TSA1, TSA2 and TSA3 for writing respectively, the blood pressure BP, the temperature T and the drugs D to be administrated to a patient. In this example, the drug administration chart comprises several rows, each row being dedicated to a given drug. The drugs are identifiable by a name or code preprinted or to be handwritten in regard of each row. The form further comprises at least one patient identification area (PIA) for specifying the patient identity (for example, name, age, size, identification number, etc.) and a sheet identification area (SIA), especially, to distinguish two sheets of a same patient (for example, by a date). Other areas A can be provided for specifying other information such as, for example, the identity of the medical staff, of the hospital, etc.

Such a conventional observation sheet is adapted to the invention by printing on or with the form, specific pattern(s) adapted to a digital pen localization system. This can be done by scanning an existing observation form and printing again this form with a pre-printed "engrained" pattern page. The engrained form can also be directly generated by a computer.

A model of the form is preferentially stored in the computerized system to be displayed with all the written information recorded by the digital pen.

The model is used to transfer the printed scale of time of the time scaled blank charts into the computerized system in order to render the system able to determine, on the basis of the coordinates of a mark, the corresponding time. One of the contributions of the invention is, in the generation of the model, the adding of information relating to the scale of time of the time scaled areas. The above steps constitute a preparation phase that has to be made only once for each kind of observation form.

The information written on a given printed form have to be distinguishable from information written on another form of the same kind. The preprinted forms have to be identifiable individually in the computerized system, for further processing, storage, sorting, etc. The requirement is then that, before the first writing of information on a given form of a patient, the medical staff does a specific action for associating this form to a given patient. For instance, the system identifies with a conventional character recognition method, the name of the patient written in a dedicated box of the form filled by the medical staff along with the first use of the form sheet.

Each printed form comprises an individual background pattern which allows the system to not only localize the tip on the page but also to identify the printed form with respect to other of a same model. Then, the registered information can be processed in relationship with the correct support in the computerized system.

Figure 2:
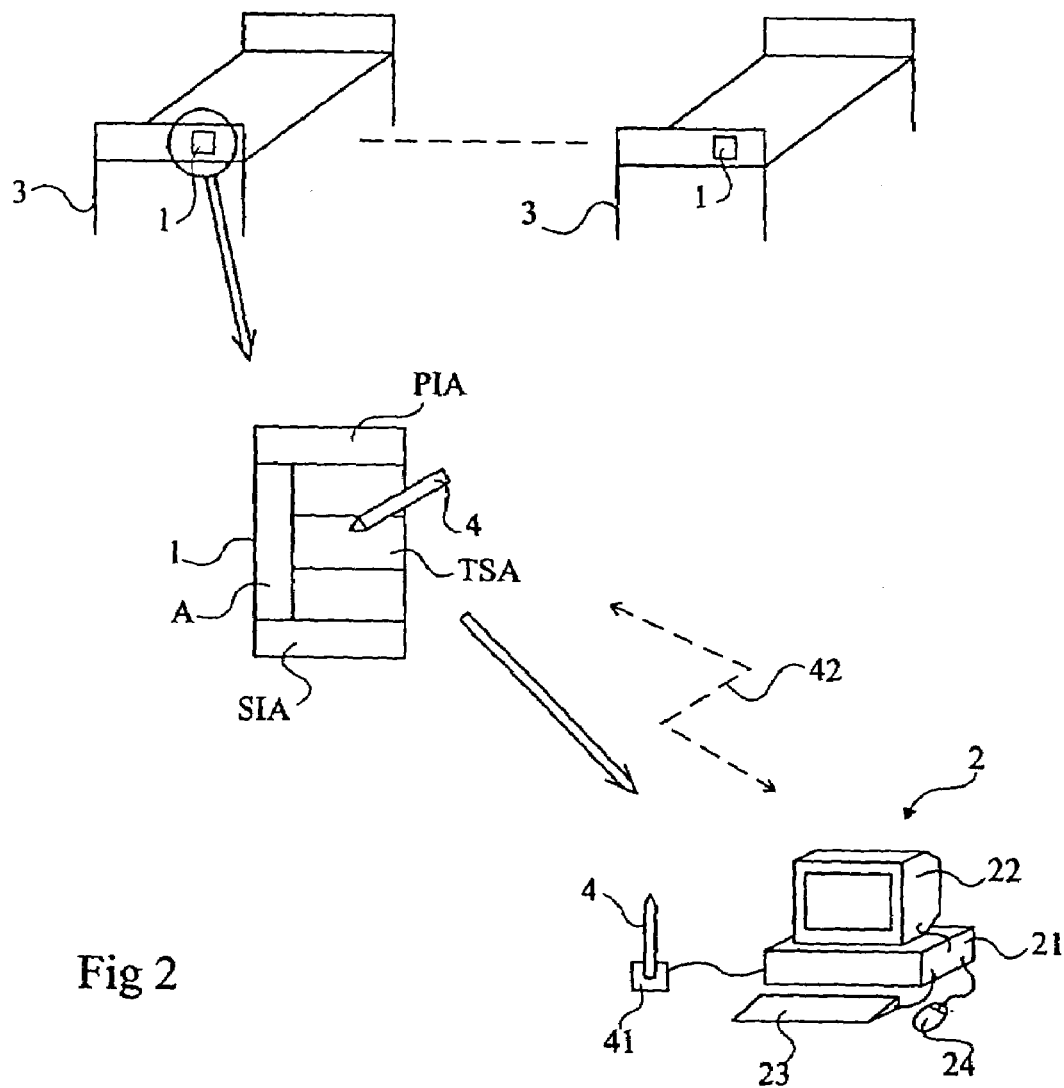
FIG. 2 illustrates, very schematically, an information entering mode according to the present invention.

FIG. 2 illustrates an embodiment of the method according to the invention.

In this example, preprinted observation forms 1 are attached to beds 3, for example in a hospital.

The medical staff uses, for entering and/or updating information on the forms, digital pens 4 having also a usual tip. Hence, the information are registered digitally and written conventionally on the forms.

According to one embodiment, the pen 4 comprises storage means to temporarily store the data until it is associated to a socket 41 linked to a computer 2 for downloading the data. In FIG. 2, the computer 2 is represented in a simplified way by a central unit 21, a screen 22 and input devices 23 and 24 (for example, a keyboard and a mouse). According to another embodiment, the digital pen directly communicates with the computer through a wireless link 42.

The data handwritten on the forms 1 are available to the medical staff for conventional uses. However, the same data are, according to the invention, available in the computer 2 for various purposes. For example, the observation charts are then available for:

transmission to a distant computer for being examined by a doctor or other medical staff;

generation of an alert if a value of a parameter passes a threshold defined by the doctor for this patient or in a general way;

docketing into the digital medical folders of the patients; and/or statistical analysis, etc.

Further, according to the invention, the data relating to observation charts are automatically processed for interpreting time information handwritten during the updating.

According to a first aspect, the time information corresponds to the updating of time scaled areas TSA. The system determines, by interpreting the location of the handwritten data in each area TSA, the printed time corresponding to the column wherein or on which the data is written. Then, the system compares this printed time to the writing/recording time noted when the digital pen stores data. As any computerized means, the digital pen and the computer have clocks convertible into universal time. The comparison gives information on the consistency of both times. In some cases, an inconsistency between the recording time and the printed time is not critical for the patient, for example if it is due to a delayed updating of the observation charts. In other cases, time inconsistency may signify an error of the medical staff when updating the form or an error in the time of some action (like a drug administration). Such an error may have critical consequence for the patient.

Hence, in case of inconsistency, several actions can be taken depending on the application. For example, a detected inconsistency can lead to:

a suppression of the inconsistent information from the digital record of the patient folder;

an alert signal to the medical staff, especially to allow him checking a possible error in the handwritten information or in a taken action; and/or a specific marking in the registered information.

It is to be noted that a given pen used to write information is itself identifiable, so that the registered information can be stored with an identification of the person who wrote it. Such identification can be used, for example, for directing the alert messages.

According to a second aspect, the time information is automatically compared to ore-established or prescript timings. For example, the temporal data of drug administration is automatically compared to the timing provided in the drug prescription by the doctor. According to another example, the doctor prescripts (eventually individually for each patient) that an action (for example, temperature measurement) has to be taken with a given periodicity or at given times. In the following, this aspect will be disclosed in connection to drug administration but also applies to any other action.

The comparison with respect to a prescript time can be made either on the basis of the recording time, or printed time, or current time.

Such a comparison can lead to automatically detecting a miss in the drug administration for, for example, alerting the medical staff for correcting the miss or taking into account this miss for further interpreting the effects of the drug.

According to this aspect, the prescriptions are digitalized, either as being directly inputted in the computer or as being interpreted in a time scaled drug prescription area of a form, using a digital pen. The interpretation of such time scaled prescription area can then be done automatically.

An advantage of the present invention is that it combines the conventional way of filling observation charts with a computerized processing of the information, without involving for the medical staff drastic changes of its habits.

Another advantage of the present invention is that eventual errors in the time of entering information can be detected. Hence, the reliability of observation charts is improved.

Another advantage of the present invention is the ability to make an electronic audit trail of all changes to medical charts or other such handwritten medical notes. This will enable the system operators to detect medical fraud relating to notes being changed after a medical incident.

Another advantage is that an eventual miss of prescript actions can be automatically detected and forwarded to any determined person.

Another advantage of the present invention is that the digital registering of drug prescription and drug administration renders possible to improve the efficiency of drug stock management.

The practical implementation of the invention is, on the basis of the above functional explanations, in the ability of one with an ordinary skill in the art using conventional tools.

The computerized tools for the implementation of the invention may use databases or storage media which are remote (for example accessible through Internet) from the computer receiving information from the pen. Further, more than one computer can be used for collecting the information in several locations of a same hospital or the like.

Of course, the orientation of the charts can be modified, the term column being used to define a printed line of points having the same projection on the printed time axis, whatever is its direction. Reference has been made to printed times, but it includes printed periods of time. Further, the printed time axis can be discontinuous and/or the times of the columns can correspond to events (for example, wake-up time, lunchtime, bedtime).

Having thus described at least one illustrative embodiment of the invention, various alterations modifications and improvements will readily occur to those skilled in the art. Such alteration, modification, and improvements are intended to be within the spirit and scope of the invention. Accordingly, the foregoing description is by way of example only and is not intended to be limiting. The invention is limited only as defined in the following claims and the equivalent thereto.

The invention claimed is:

1. A method for digitally processing information to be written on an observation form, said form being preprinted with at least one blank time scaled area chart having at least one line and several columns, each column corresponding to a determined printed time, said form being also preprinted with a pattern adapted to cooperate with a digital pen and a computerized localization system for determining the position of the pen, the method comprising:

using a pen having a writing tip and a digital tip;
filling in data in one column at a time;
reproducing said data in the computerized localization system and associating to said data its recording time;
comparing said recording time with the localized printed time of said data, so as to detect any inconsistency between the recording time and the printed time; and
comparing the recording time and/or the localized printed time and/or the current time with a preregistered prescript time of a given prescript action monitored by said chart, so as to detect an eventual miss of the prescript action, wherein said prescript time is automatically deduced from another chart.

2. The method of claim 1, further comprising generating an alert if a difference between said localized printed time and said recording time exceeds a predetermined threshold.

3. The method of claim 1, in which said prescript action is a drug administration.

4. The method of claim 1, further comprising collecting information on drug administration from several observation forms for drug stock evaluation.

5. A computerized system for processing information to be written on at least one printed observation form, said form being preprinted with at least one blank time scaled area chart having at least one line and several columns, each column corresponding to a determined printed time, said form being also preprinted with a pattern adapted to cooperate with a digital pen and a computerized localization system for determining the position of the pen, the system comprising:

at least one pen having a writing tip and a digital tip;
means for registering along with data handwritten in one column at one time, its recording time;
means for collecting and storing said data and recording time, and for comparing said recording time with the localized printed time of said data, in order to detect a possible inconsistency between both times; and
means for collecting information on drug administration from several observation forms for drug stock evaluation.

6. The system of claim 5, further comprising means for comparing the recording time and/or the localized printed time and/or the current time with a preregistered prescript time of a given prescript action monitored by said chart, so as to detect an eventual miss of the prescript action.

7. The system of claim 6, wherein said prescript time is automatically deduced from another chart.

8. The system of claim 7, further comprising means for generating an alert if a difference between said localized printed time and said recording time exceeds a predetermined threshold.

9. The system of claim 7, wherein said prescript action is a drug administration.

10. The system of claim 7, wherein the system is operable to identifying a person that filled in data in at least one column and subsequently send an alert message to said person when the inconsistency between the recording time and the localized printed time is detected.

11. A method for digitally processing information to be written on an observation form, said form being preprinted with at least one blank time scaled area chart having at least one line and several columns, each column corresponding to a determined printed time, said form being also preprinted with a pattern adapted to cooperate with a digital pen and a computerized localization system for determining the position of the pen, the method comprising:

reproducing data filled in one column at a time with said pen in the computerized localization system and associating to said data its recording time; and
comparing the recording time and/or a localized printed time of said data and/or the current time with a preregistered prescript time of a given prescript action monitored by said chart, so as to detect an eventual miss of the prescript action, wherein said prescript time is automatically deduced from another chart.

12. The method of claim 11, further comprising collecting information on drug administration from several observation forms for drug stock evaluation.

13. The method of claim 11, further comprising comparing said recording time with a localized printed time of said data, so as to detect any inconsistency between the recording time and the printed time.

14. The method of claim 13, further comprising generating an alert if a difference between said localized printed time and said recording time exceeds a predetermined threshold.

15. The method of claim 11, wherein said prescript action is a drug administration.

16. The method of claim 11, further comprising identifying a person that filled in data in at least one column.

17. The method of claim 16, further comprising sending an alert message to said person when the inconsistency between the recording time and the localized printed time is detected.

18. A method for digitally processing information to be written on an observation form, said form being preprinted with at least one blank time scaled area chart having at least one line and several columns, each column corresponding to a determined printed time, said form being also preprinted with a pattern adapted to cooperate with a digital pen and a computerized localization system for determining the position of the pen, the method comprising:

using a pen having a writing tip and a digital tip;
filling in data in one column at a time;
reproducing said data in the computerized localization system and associating to said data its recording time;
comparing said recording time with the localized printed time of said data, so as to detect any inconsistency between the recording time and the printed time;
comparing the recording time and/or the localized printed time and/or the current time with a preregistered prescript time of a given prescript action monitored by said chart, so as to detect an eventual miss of the prescript action; and
comprising collecting information on drug administration from several observation forms for drug stock evaluation.

19. A computerized system for processing information to be written on at least one printed observation form, said form being preprinted with at least one blank time scaled area chart having at least one line and several columns, each column corresponding to a determined printed time, said form being also preprinted with a pattern adapted to cooperate with a digital pen and a computerized localization system for determining the position of the pen, the system comprising:

at least one pen having a writing tip and a digital tip;
means for registering along with data handwritten in one column at one time, its recording time;

means for collecting and storing said data and recording time, and for comparing said recording time with the localized printed time of said data, in order to detect a possible inconsistency between both times; and means for comparing the recording time and/or the localized printed time and/or the current time with a pre-registered prescript time of a given prescript action monitored by said chart, so as to detect an eventual miss of the prescript action, wherein said prescript time is automatically deduced from another chart.

* * * * *

UNITED STATES PATENT AND TRADEMARK OFFICE
CERTIFICATE OF CORRECTION

PATENT NO. : 7,167,166 B1 Page 1 of 1
APPLICATION NO. : 10/632588
DATED : January 23, 2007
INVENTOR(S) : Ben Burdsall et al.

It is certified that error appears in the above-identified patent and that said Letters Patent is hereby corrected as shown below:

On the Title Page

In column 1, before item (21), under "(*) Notice:" after "U.S.C. 154(b) by" delete "420" and substitute --424-- in its place.

In the Specification

In column 3, line 56, before "The ordering of the drugs" delete "drug." and substitute --drugs.-- in its place.

In column 5, line 62, after "automatically compared to" delete "ore-established" and substitute --pre-established-- in its place.

In column 6, line 55, immediately after "invention, various alterations" insert --,-- (comma).

Signed and Sealed this

Twenty-fourth Day of April, 2007

JON W. DUDAS
*Director of the United States Patent and Trademark Office*